(12) United States Patent
Warkentine et al.

(10) Patent No.: US 8,092,400 B2
(45) Date of Patent: Jan. 10, 2012

(54) CALCULATING THE POSITION OF BODY PARTS, TAKING INTO ACCOUNT ANATOMICAL SYMMETRY

(75) Inventors: Blaine Warkentine, Royersford, PA (US); Herr Hansjörg Huber, Feldkirchen (DE)

(73) Assignee: BrainLAB AG, Feldkirchen (DE)

( * ) Notice: Subject to any disclaimer, the term of this patent is extended or adjusted under 35 U.S.C. 154(b) by 164 days.

(21) Appl. No.: 12/388,711

(22) Filed: Feb. 19, 2009

(65) Prior Publication Data
US 2009/0227905 A1 Sep. 10, 2009

Related U.S. Application Data

(60) Provisional application No. 61/032,244, filed on Feb. 28, 2008.

(30) Foreign Application Priority Data

Feb. 21, 2008 (EP) .................................... 08151747

(51) Int. Cl.
*A61B 5/103* (2006.01)
*A61B 5/117* (2006.01)

(52) U.S. Cl. ....................... 600/595; 600/587
(58) Field of Classification Search .......... 600/587–595; 702/127, 150–153
See application file for complete search history.

(56) References Cited

U.S. PATENT DOCUMENTS

| | | | |
|---|---|---|---|
| 3,879,849 A * | 4/1975 | Schwartz et al. | 433/3 |
| 6,895,341 B2 * | 5/2005 | Barrey et al. | 702/32 |
| 2005/0004495 A1 * | 1/2005 | Goswami | 600/595 |
| 2007/0161929 A1 | 7/2007 | Maier | |

FOREIGN PATENT DOCUMENTS

| | | |
|---|---|---|
| DE | 693 19 212 T2 | 11/1998 |
| EP | 1 788 581 | 5/2007 |

* cited by examiner

*Primary Examiner* — Jeffrey G Hoekstra
(74) *Attorney, Agent, or Firm* — Renner, Otto, Boisselle & Sklar, LLP

(57) ABSTRACT

The present application relates to a method for determining the position or relative position of body parts, taking into account the anatomical symmetry, wherein at least one first-side body part is provided on the first side of an anatomical body, and at least one second-side body part is provided on the second side of the anatomical body, wherein the first side is separated from the second side by a body symmetry plane, said method comprising the steps of: providing first-side body part data which describes or implies the position of the at least one first-side body part; providing second-side body part data which describes the position of the at least one second-side body part; providing symmetry plane data which describes the position of the body symmetry plane; calculating the mirrored position or mirrored positions of the at least one second-side body part which results after the position of the at least one second-side body part has been mirrored on the body symmetry plane, on the basis of the second-side body part data and the symmetry plane data, and determining and/or displaying a deviation between the mirrored position or positions of the at least one second-side body part and the position or positions of the at least one first-side body part; and/or determining a mirrored relative position of the second-side body parts, on the basis of the second-side body part data and the symmetry plane data.

7 Claims, 3 Drawing Sheets

CALCULATING THE POSITION OF BODY PARTS, TAKING INTO ACCOUNT ANATOMICAL SYMMETRY

RELATED APPLICATION DATA

This application claims the priority of U.S. Provisional Application No. 61/032,244, filed on Feb. 28, 2008, which is hereby incorporated in its entirety by reference.

FIELD OF THE INVENTION

The present invention relates to determining the position of body parts which are connected to a joint of an anatomical body, for example of a human or animal. The joint can for example be a knee joint, a shoulder joint, a hip joint, etc. These joints each have the property that there is a left joint and a right joint which exhibit symmetrical kinematics, i.e. in the ideal case of a healthy body, the possible movement trajectories are symmetrical, in particular with respect to a symmetry plane and/or symmetry axis. The invention uses the kinematic symmetry of the joints to deduce—from the position of body parts which are connected to a joint on one side of the body—a possible or desired position of body parts which are connected to the joint which is symmetrical to it on the other side of the body part. With respect to the kinematics of the joints, reference may be made to the standard work by I. A. Kapandji "The Physiology of the Joints", in which the human biomechanics, including the kinematics, of the joints is described.

The present invention also relates not only to using anatomical symmetry to the extent that it relates to the kinematics of the movement, but also or alternatively relates to using anatomical symmetry to the extent that it relates to the static position of the body parts. In particular, the static symmetry is used to determine the position of body parts or the relative position of body parts. In the ideal case, the anatomical body is symmetrical with respect to a symmetry plane, the median sagittal plane. On the basis of this ideal assumption, it is possible to calculate the position of a body part which it would occupy, given an ideal symmetry. It is also possible to calculate what the relative position of the body parts would look like, given an ideal anatomical (static) symmetry.

BACKGROUND OF THE INVENTION

A method for determining the femoral anchorage point of a cruciate knee ligament is described in European patent specification DE 693 19 212 T2. Measuring an antetorsion angle of a femur is known from US 2007/0161929 A1 and EP 1 787 581 A1. Reference is also made to these documents, which are hereby incorporated into the disclosure, with respect to determining axes and orientations of a body part and assigning reference frames to a body part.

SUMMARY OF THE INVENTION

It is an object of the invention to determine the position or relative position of body parts, taking into account the anatomical symmetry of an anatomical body which is given in the ideal case.

It is in particular an object of the invention to determine the position which a body part occupies or would occupy if the joint connected to it had kinematics which are symmetrical with respect to the corresponding joint arranged on the other side of the body.

The above object is solved by the subjects of the independent claims. Advantageous developments follow from the sub-claims.

The invention is in particular intended to assist in identifying and quantifying misplacements of body parts which follow from anatomical symmetry observations. It is then of course left to the physician to assess whether there is a misplacement and which of the two sides of the body has a misplacement and which side represents a healthy placement. The invention can also help in assessing relative placements of body parts. It is for example possible to compare the extent of a varus or valgus on one side of an anatomical body with the extent of a varus or valgus on the other side. It is also for example possible by means of the invention to compare the maximum abduction of the femur on one side with the maximum abduction of the femur on the other side. It is in particular possible to determine where a body part would be situated after a movement about a joint, if it behaved symmetrically with respect to the body part which anatomically corresponds to it.

The invention relates to calculating the position or relative position of body parts, using symmetry rules. The symmetry rules are based in particular on providing data (symmetry plane data) which determines or implies the position of a symmetry plane of the body—also referred to here as a body symmetry plane—in particular relative to the body parts and/or in a common reference frame. The position of a symmetry plane is in particular implied if it is presupposed that two anatomically corresponding body parts (for example, a left and right upper leg), the position of which is described by body part data (see below), are arranged symmetrically with respect to the symmetry plane, wherein a first-side body part is a body part which lies on one of the two sides of the anatomical body which are separated by the body symmetry plane. The second-side body part lies on the other side. First-side body part data describes the position of the at least one first-side body part. The invention can thus be applied to one, two, three or more body parts on each side. The second-side body part data correspondingly describes the position of the at least one second-side body part. The position of a body part or of two or more body parts is preferably mirrored on the body symmetry plane. Preferably, the mirrored position of a second-side body part is compared with the position of the first-side body part which anatomically corresponds to the second-side body part. In particular, a deviation between the mirrored position of the second-side body part and the position of the anatomically corresponding first-side body part is determined and/or displayed. It is in particular displayed overlapping, such that both the mirrored position of the second-side body part and the non-mirrored position of the first-side body part are visible to the observer. They can be displayed simultaneously, or the observer can switch back and forth between the two images, or they are for example arranged next to each other.

In addition to or as an alternative to comparing a non-mirrored position with a mirrored position, the positions of at least two second-side body parts are compared with each other; to this end, a relative position of the at least two second-side body parts is in particular determined or provided. The determination of the mirrored relative position is based on the second-side body part data and the symmetry plane data.

The aforesaid determination of the mirrored relative position can be made in various ways. For example, the position of a first second-side body part can be mirrored and the position of a second second-side body part can likewise be mirrored. The relative position between the mirrored position of the first second-side body part and the mirrored position of the second second-side body part is then calculated. This is then the mirrored relative position. As an alternative to this, a relative variable can be determined which describes the relative position of the first second-side body part relative to the second second-side body part (on the second side of the body symmetry plane). This relative variable can for example be a vector or can also be two vectors. In the case of two vectors, one vector for example links the starting points of a distance which describes the position of the second-side body parts, and the second vector links the end points of a distance which describes the position of the second-side body parts. This vector or these vectors are then mirrored on the symmetry plane. The mirrored vector or vectors then represent the mirrored relative position.

The relative position can describe not only the relative position between two different body parts, but also the relative position which one and the same body part occupies when it has two different placements (positions). One position can for example represent the position of the lower leg when the leg is extended, and the other position can represent the position of the lower leg during flexion (for example, 90° flexion). The body part (lower leg) thus occupies two different placements. The relative position between these two different placements is also referred to here as the "placement relative position". Preferably, a mirrored placement relative position is calculated in accordance with an embodiment. This can for example be performed such that the position of the body part in a first placement is mirrored, and the position of the body part in a second placement is likewise mirrored. The two different mirrored positions, which represent the body part in two different mirrored placements, have a position relative to each other which represents the mirrored placement relative position. In accordance with another approach, the relative position between two placements of the body part can be described by a relative variable, which is for example one or more vectors such as have already been illustrated above. This relative variable (vector or vectors) is then mirrored on the symmetry plane. The mirrored relative variable then describes the mirrored placement relative position. In accordance with an embodiment, the placement relative position mirrored onto one side can then for example be compared with the placement relative position which is given on this side, so as to determine deviations from an ideal anatomical symmetry. In accordance with a particular embodiment, it is in particular possible to determine, on the basis of the mirrored placement relative position, how the anatomically corresponding body part (for example, the left upper leg) would behave when transitioning from a first placement to a second placement, if it underwent the movement—mirrored on the body symmetry plane—of the anatomically corresponding body part on the other side of the body. To this end, one or two vectors are for example positioned on the (first-side) body part which describe the mirrored placement relative position. One vector is for example positioned at the start of a distance which represents the position of the body part, while the other vector is positioned at the end of this distance. If the tips of the vectors are then connected, this results in a distance which represents the placement of the body part if it behaved exactly like the anatomically corresponding body part when moving. Due to the particular importance of this aim, an independent claim is additionally directed to it. The corresponding embodiment is illustrated further below.

The placement of the body part which is determined in this way can then in turn be compared with the actual placement of the body part. It is thus in particular possible to identify differences in the movement trajectories or in the placement relative positions between one side of the body and the other.

In one of the embodiments, calculating the mirrored position or positions and/or the mirrored relative positions includes the step of projecting the position or relative position into a plane. This plane is referred to here as the projection plane. If, for example, the varus or valgus of a leg is of interest, then this can be described by a relative variable. The relative variable is in particular an angle which is formed between the lower leg and the upper leg when the leg is extended. This angle can then for example be determined from the positions projected into the projection plane. The so-called frontal plane or coronal plane, which is perpendicular to the sagittal plane, is preferred in this case as the projection plane. The projected position can then be mirrored on the body symmetry plane. It is for example also possible to take a different approach, such as mirroring the non-projected positions first and then projecting the mirrored positions into the projection plane. A relative variable—such as for example the angle between the two body parts in the projection plane—is then in particular determined.

The position of a body part is for example represented by a distance, as already mentioned. The end points of the distance can for example be determined using landmarks. The position of a body part can also be described by characteristic axes, such as for example a tibial axis, or by planes, for example a plane which virtually lies on the acetabulum. Finally, a generic model of the body part or three-dimensional body part data, which is acquired by means of magnetic resonance or a three-dimensional x-ray recording (CT), can also be used to describe the position of the body part.

The invention is in particular intended to be used in planning incisions into a body part, in particular bones, for example in planning incision locations such as the location of an anchorage point or the location of a drilling in the body part. It is in particular intended to help in planning incisions which have an effect on the subsequent kinematics of the joint connected to the body part, such as for example a cruciate ligament operation or implanting artificial joints. In the latter case, the body parts connected to the joint are at least partially artificial and not natural.

One advantage of the invention is that by examining the kinematics of a healthy joint, in particular on the basis of relative placements which body parts of a healthy joint occupy, it is possible to deduce desired kinematics—in particular, desired relative placements (nominal relative placements or nominal neutral placements)—of body parts which are connected to a diseased joint and therefore do not (inherently) occupy or do not stably occupy one or more desired relative placements. Advantageously, the non-ideal kinematics of a diseased joint can be identified and/or prevented from resulting in the operation being incorrectly planned, in particular in the incision location being incorrectly determined. It is also possible to identify when the body parts occupy a relative placement (for example, the so-called "anterior drawer" in the case of a cruciate ligament rupture) which does not correspond to that of a healthy joint.

Using the present invention, it is advantageously possible—after an operation—to check whether the kinematics achieved by the operation for the joint operated on correspond to the desired kinematics, wherein the kinematics can advantageously be described and measured by at least two, preferably three or more relative placements.

The method in accordance with the invention serves to calculate the position of body parts which are connected to kinematically symmetrical joints. The flexion-extension movement of the left knee joint is for example symmetrical with respect to the flexion-extension movement of the right knee joint. Raising the left upper arm outwards and to the left is for example symmetrical with respect to raising the right upper arm outwards and to the right. The median sagittal plane of the anatomical body can in particular be adduced as a symmetry plane (body symmetry plane), in order to deduce—from the relative position of two body parts connected to a joint—the position, symmetrical to it, of the body parts which are connected to the joint on the other side of the body. Kinematically symmetrical joints of a body are thus given if the body parts connected to the two joints (one joint on each side of the body, respectively) exhibit a symmetrical movement trajectory when the two joints are actuated in order to achieve an identical movement (for example, flexion, extension; adduction, abduction; internal rotation, external rotation; inclination, reclination, etc.).

In the following, one side of the body, i.e. for example the side on the left of a symmetry line or plane, for example the median sagittal plane, is referred to as the first side, and the other side of the body, i.e. for example the side on the right of the symmetry line or plane, for example the median sagittal plane, is referred to as the second side. The first side can thus relate to the left or right, and the second side to the other side in each case. The kinematics of the joint on the first side are symmetrical with respect to the kinematics of the corresponding joint on the second side, in the case of an ideally healthy body.

Using the method in accordance with the invention, it is advantageously possible to calculate the position of a body part on a first side, i.e. a first-side body part (for example, the left lower leg), in particular by calculating the position or relative position of the body parts on the other side of the body, i.e. the second-side body parts (for example, the right upper and lower leg), which are connected to the second-side joint, for example the right knee joint.

Examples of a first and second first-side body part are the left upper and lower leg. Examples of a first and second second-side body part are the right upper and lower leg. The first-side body parts are connected by a first-side joint, i.e. for example the left knee joint. There is a symmetrical second-side joint with respect to this first-side joint, i.e. for example the right knee joint. In particular, there is an anatomical correspondence (symmetrical anatomical function) between the first first-side body part and the first second-side body part (for example, both are an upper leg). In particular, there is also an anatomical correspondence between the second first-side body part and the second second-side body part (for example, they are both lower legs).

For rotational movements, for example an external rotation and internal rotation of the arm or leg, a symmetry axis which passes along, for example through, the leg is preferably determined, in order to then derive the corresponding symmetrical movement from this, wherein it is in particular the case that an external rotation on one side corresponds to an external rotation on the other side. The same applies to the internal rotation.

In accordance with the invention, second-side relative position data is advantageously provided which describes the position of the first second-side body part, for example the right upper leg, relative to the second second-side body part, for example the right lower leg. The relative position data preferably describes this relative position for at least two relative placements of the second-side body part, which are therefore also called second-side relative placements. One example of this is the full extension, i.e. 0° flexion, of the right leg as the first second-side relative placement and a 90° flexion of the right leg as the second second-side relative placement. A third second-side relative placement would for example be a 30° flexion. The relative position data can be described in a reference frame which lies in a first body part, wherein the position of the second body part is described in this reference frame. The relative position data can also be described in another reference frame which for example lies in the operating theatre or in the reference frame of a marker detection device such as is used in a surgical navigation system (IGS, image-guided surgery). The relative position data can describe not only the relative position of the body parts but also the (absolute) position of at least some of the body parts in the reference frame. They can in particular include: the first-side and second-side relative position data, the positions of the first and second first-side and second-side body parts for the first and second second-side relative placement and for the first first-side relative placement and the position of the first first-side body part in the second first-side relative placement, as well as the position of a body symmetry plane.

The relative position data is preferably determined using markers which have a predetermined, in particular known fixed position with respect to each of the first body part and the second body part. The markers can be active or passive markers which for example passively reflect electromagnetic waves, in particular light, in particular infrared light or ultrasound waves, or emit such waves, wherein a marker device consisting for example of three or more markers (for example, a reference star) is for example connected to one body part and another marker device is connected to the other body part. The connection can be non-invasive, i.e. a flexible marker strap with markers attached to it can for example be wound around a body part, for example the upper leg or lower leg. Alternatively or additionally, individual markers can also be adhered onto the upper leg. This is in particular preferable if said body parts are healthy body parts which are not to be operated on. For the body parts which are to be operated on, a marker device which is fixedly connected to the respective bone and for example screwed into the bone is preferably, but not compulsorily, provided. Preferably, landmarks on the body part are additionally measured, for example by means of pointers or a navigated instrument, which preferably likewise comprise markers and likewise represent an example of a marker device. Two or more markers are for example attached to a pointer, wherein their position relative to the pointer tip is known.

When determining the deviation between a position or relative position and an ideally symmetrical situation, non-invasive markers such as marker straps or individual markers which can in particular be adhered on the skin are preferably used, so as to burden the patient as little as possible.

Preferably, first-side relative position data is also provided which describes the position of a first first-side body part, i.e. for example the left upper leg, in a first first-side relative placement, i.e. for example in full extension (0° flexion), relative to a second first-side body part, for example the left lower leg. This relative position data is preferably likewise detected by detecting a reference star or individual markers (for example two, three or more) attached to the first and/or second first-side body part, and/or by detecting landmarks by means of pointers or a navigated instrument. The relative position data is preferably determined by marker detection (reference star and/or pointers) if there is a good probability that the position of the body parts in the first first-side relative placement is not impaired by the disease of the joint, i.e. the position of the first second-side body part relative to the second second-side body part, i.e. for example the right upper leg relative to the right lower leg, is not impaired by the disease. The extension of the leg is cited here as an example in the case of a cruciate ligament rupture. The cruciate ligament rupture impairs the relative position during flexion, but has no effect on the relative position of the left upper leg and left lower leg in full extension. In particular when such a reliable relative placement is not given, the relative position of the first-side body parts in the first first-side relative placement can be deduced from the relative position of the two second-side body parts in a first second-side relative placement by referring to the second-side relative position data and taking into account the symmetry, without measuring the relative position of the first-side body parts in the first first-side relative placement, for example by marker detection. The position of the first first-side body part relative to the second first-side body part, which is described by the first-side relative position data, can be described in any reference frame, for example in a reference frame which lies in the operating theatre or in the reference frame of the aforesaid navigation system. The relative position of the two first-side body parts can in particular also be described in a reference frame which lies in one of the two body parts. In the following, it is assumed that the first-side relative position data determined by marker detection relates to the first first-side relative position. Its is therefore also called the first first-side relative position data. It is also assumed that second and subsequent first-side relative position data relates to the second and subsequent relative placements and is calculated on the basis of the second-side relative position data (without marker detection).

Thus, the first first-side relative position data can, as stated above, be determined by detecting marker devices, for example a reference star and/or pointers. In accordance with an alternative embodiment, however, the first first-side relative position data is also calculated from the first second-side relative position data which relates to the first second-side relative placement, using symmetry considerations. The position of the first and second second-side body part (for example, in the reference frame of the navigation system) is for example mirrored, for example on the median sagittal plane, so as to calculate the position of the first and second first-side body part in the first relative placement. The relative position of the two first-side body parts in the first first-side relative placement can then also be calculated from this calculated position (see below). The result of the calculation can then for example also be compared with the detected position of the first and/or second first-side body part, whereby deviations between the arrangement of body parts and the ideally symmetrical arrangement can be identified. This can also be performed in accordance with the invention for a single relative placement, such that in this variant of the invention, the calculations relating to the second relative placement are not necessary. Relative placements calculated in accordance with the invention, more specifically the calculated relative position of the first-side body parts in the second first-side relative placement (calculated for example in the way described above), can also be compared with detected positions of the first-side body parts in the second first-side relative placements, whereby deviations between the first-side relative placements and the second-side relative placements, which may in particular be attributed to a deviation between the kinematics of the first-side joint and the kinematics of the second-side joint, can be identified. This can in particular be used to identify diseased joints and/or check the result of an operation.

Preferably, the first first-side relative placement is symmetrical with respect to the first second-side relative placement, and the second first-side relative placement is symmetrical with respect to the second second-side relative placement. Positions of the body parts are linked to the respective relative placements. These positions are preferably determined for the first first-side relative placement, the first second-side relative placement and the second second-side relative placement by means of a detection device, i.e. they are based on detection signal data.

In accordance with the invention, the position of the first first-side body part relative to the second first-side body part in the second first-side relative placement is preferably calculated from the first-side and second-side relative position data, i.e. for example, the relative position of the left upper leg and lower leg at 90° flexion is calculated from the relative position of the left upper leg and lower leg at 0° flexion (full extension) and from the relative position of the right upper leg and lower leg at 0° flexion and 90° flexion.

A pivot angle (for example, 90°), by which the second second-side body part (for example, the right lower leg) pivots relative to the first second-side body part (for example, the right upper leg) when transitioning from the first second-side relative placement (0° flexion) to the second second-side relative placement (90° flexion), is for example determined from the second-side relative position data. Preferably, the second first-side body part (for example, the left lower leg) is then pivoted relative to the first first-side body part (for example, the left upper leg) by the same pivot angle (for example, 90°), starting from the first relative placement (for example, 0° flexion), so as to calculate the position of the second first-side body part (for example, the left lower leg) in the second first-side relative placement (90° flexion).

When determining the second first-side relative placement, symmetry rules are preferably taken into account which describe the kinematic symmetry of the joint movement. To this end, at least one second-side relative vector is for example mirrored on a body symmetry plane, in particular on the median sagittal plane. At least one second-side relative vector, which describes the transition from the first second-side relative placement to the second second-side relative placement, is for example broken down into components, for each of which a symmetry rule is applied. The vector can for example exhibit a component in a plane which is parallel to the median sagittal plane, which is referred to as the parallel component, and a component which is perpendicular to the median sagittal plane, which is referred to as the perpendicular component. It is possible to apply, to the parallel component, the symmetry rule that it is adopted non-mirrored for a first-side relative vector. For the perpendicular component, it is possible to apply the symmetry rule that it is mirrored on the median sagittal plane. Adding the parallel component and the mirrored perpendicular component produces the first-side relative vector which describes the transition from the first first-side relative placement to the second first-side relative placement. Preferably, two second-side relative vectors are determined for the first second-side body part which are for example positioned at defined points, for example at two points on the body part which are defined by landmarks. First-side relative vectors are then determined from these which are symmetrical to them and positioned at the corresponding points on the first first-side body part and describe the transition.

The first-side and second-side relative position data has preferably also been acquired in a position or determined for a position in which the first first-side body part and the first second-side body part are arranged symmetrically with respect to each other relative to the median sagittal plane. The first-side and second-side relative vectors are then preferably determined and/or applied on the basis of this presupposition or assumption.

It is not compulsory to determine or provide the position of the median sagittal plane. Thus, even without determining the median sagittal plane, the calculations can also be based on the assumption that the movement is only performed in one plane which is parallel to the median sagittal plane, i.e. a perpendicular component does therefore not exist.

If the position of the median sagittal plane is not known (not provided), the median sagittal plane can then for example be determined by means of pointers, by tapping landmarks on the body which are typically symmetrical with respect to the median sagittal plane. If these landmarks are connected by a straight line, and a plane which is perpendicular to the line is placed halfway along it, then the plane thus obtained can be defined as the median sagittal plane. If, for example, the first first-side body part and the first second-side body part are situated in a defined placement (for example, 0° flexion) parallel to each other, the position data for the first first-side body part and the first second-side body part can also be used, so as to determine the median sagittal plane by using a virtual connection between the body parts and determining a plane which is perpendicular to the connection.

It is in particular possible to determine regions which fulfill a particular property with regard to their relative position, depending on the placement of the first first-side body part relative to the second first-side body part. It is in particular possible to determine the position relative to the second second-side region which applies to a first second-side region when the second-side joint for example performs a particular movement. In this way, it is possible to define a nominal function for the relative position of the regions. This nominal function can then be compared with the function which is given on the first side, so as for example to determine whether the second-side joint is healthy.

Examples of regions are points or regions on the surface of the body part or recesses or drillings in the body part. A relative variable provides an indication of the relative position between the first region and the second region. The calculation of the relative variable depends on the position of the first region relative to the second region. In particular, it describes a geometric relationship between the regions. Examples of relative variables are an angular relationship between straight lines or axes which pass through the regions and/or body parts, or the relative distance between the regions, or a vector which connects the two regions. In particular, one of the regions is situated on a first first-side body part, and the other region is situated on a second first-side body part.

The position of the regions can be specified in a general reference frame, for example the reference frame of the navigation system or the reference frame of the operating theatre. They can however also for example be specified in the reference frame of the body part in which the region lies. The relative variables are in particular calculated by incorporating the data concerning the relative position between the two body parts. This calculation is preferably made for the different relative placements, so as to be able to determine how the relative variable changes depending on the relative placement.

The region data which describes the relative position of the regions in the first and/or second relative placement can for example be acquired by means of pointers which are brought into contact with the respective region in the first and/or second relative placement. The pointers typically comprise at least two markers. By detecting the markers, and due to the known relative position between the markers and the pointer tip, it is then possible to determine the position of the region which is in contact with the pointer tip, for example in the reference frame of the body part in which the region is situated or in the reference frame of the navigation system. On the basis of this, the relative position between the regions is then calculated, so as to determine the region data.

In one embodiment of the invention, it is not necessary for the body parts to occupy the first and/or second first-side relative placement in order to capture the region data. It can also be captured in another relative placement which does not match the first and/or second relative placement. However, the position of the first and second first-side body part relative to their position in the first and/or second relative placement is preferably likewise known for this other relative placement. On the basis of this, the method in accordance with the invention can then calculate where the region would be situated in the first and/or second relative placement. In this way, the region data for the first and/or second relative placement is then likewise produced.

The region data can also be processed in current time, i.e. with no time lag, and it is possible to check whether it fulfills a predetermined function, i.e. it is for example possible to calculate, on the basis of the current region data which for example follows from the current position of a pointer, whether the relative variable changes during a transition from the first to the second relative placement, or whether it remains the same. It is sufficient for this purpose to detect the position of one of the two regions on one of the two first-side body parts, for example using a pointer, in any first-side relative placement. The region on the other of the two body parts is then detected, for example by means of a pointer, and a calculation is made in current time as to whether a predetermined condition is fulfilled or not. The condition can for example be that the relative variable does not change during a transition from the first to the second relative placement. The pointer can then be moved, so as to change one of the two regions. Preferably, a determination as to whether the condition is fulfilled is made in current time for each placement of the pointer. This is in particular displayed. It is for example displayed that the predetermined condition is fulfilled in the current placement of the pointer. The surgeon then knows that he has found a matching region. This is possible in accordance with the invention, without moving the body parts relative to each other. In particular, the body parts do not have to be moved in order to occupy the first and second first-side relative placements, but can occupy any other first-side relative placement, at which for example the surgeon can most easily introduce the pointer. The body parts are then moved into the first and second first-side relative placements, and the regions are detected in these placements, by calculation, i.e. virtually.

In accordance with one embodiment, the different relative placements are used to determine a movement trajectory, for example on the second side. This movement trajectory can then be converted into a nominal movement trajectory for the first side, using the method in accordance with the invention and in particular by taking into consideration symmetry rules. In particular, a movement trajectory (actual movement trajectory) for the first side can likewise be determined by measuring a plurality of relative placements of the first side, and this actual movement trajectory can be compared with the nominal movement trajectory determined by the second-side relative placements. In particular, it is possible to display if there is a deviation between the nominal movement trajectory and the actual movement trajectory.

For determining the second-side relative position data, marker devices are advantageously used which in particular are not fastened to a bone but rather preferably do not or do not substantially penetrate the skin of the body part. Preferably, a marker device is for example used which can be bound around the body part in a force fit and/or positive fit, i.e. for example a marker strap (for example, a so-called headband). Thus, the marker devices preferably do not penetrate the body part, but rather preferably maintain a fixed relative position relative to the body part by contact with the surface.

The invention is also directed to a program which performs the predetermined method, in particular using a data processing device, for example a computer. It is also directed to a storage medium, such as for example a ROM or CD, which stores the program, and to a signal wave which for example transfers the information constituting the program, for example in an internet downloading process.

The invention also relates to a navigation system which comprises a detection device for detecting markers of marker devices, for example reference stars or pointers, so as to detect the position of the body parts and/or the position of regions of the body parts. The detection device generates detection signals which are implemented by the data processing facility in order to determine the relative position data and/or region data which then forms the basis for the subsequent calculation in accordance with the methods in accordance with the invention.

DETAILED DESCRIPTION

Figure 1:
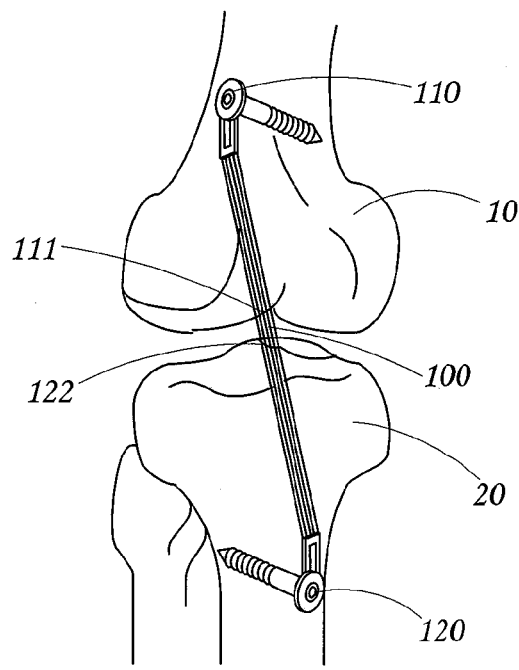
FIG. 1 shows a femur and a tibia, together with a cruciate ligament substitute.

FIG. 1 shows the joint-side end of the femur 10 and the tibia 20. A patella tendon or an implant ligament 100 which is fastened at its ends to each of the femur and the tibia via screws 110 and 120, is for example used as the cruciate ligament substitute. The ligament 100 passes through a drilling channel in the femur 10 and in the tibia 20. These drilling channels have joint-side exit openings 111 (on the femur) and 122 (on the tibia). In order to be able to substitute the function of the cruciate ligament well, it is desirable for the relative distance between the exit openings 111 and 122 to remain as constant as possible, irrespective of the degree of flexion. These exit openings 111 and 122 represent examples of the aforesaid regions for which the relative variable (the distance) is intended to be as invariable as possible, irrespective of the relative placements.

Figure 2:
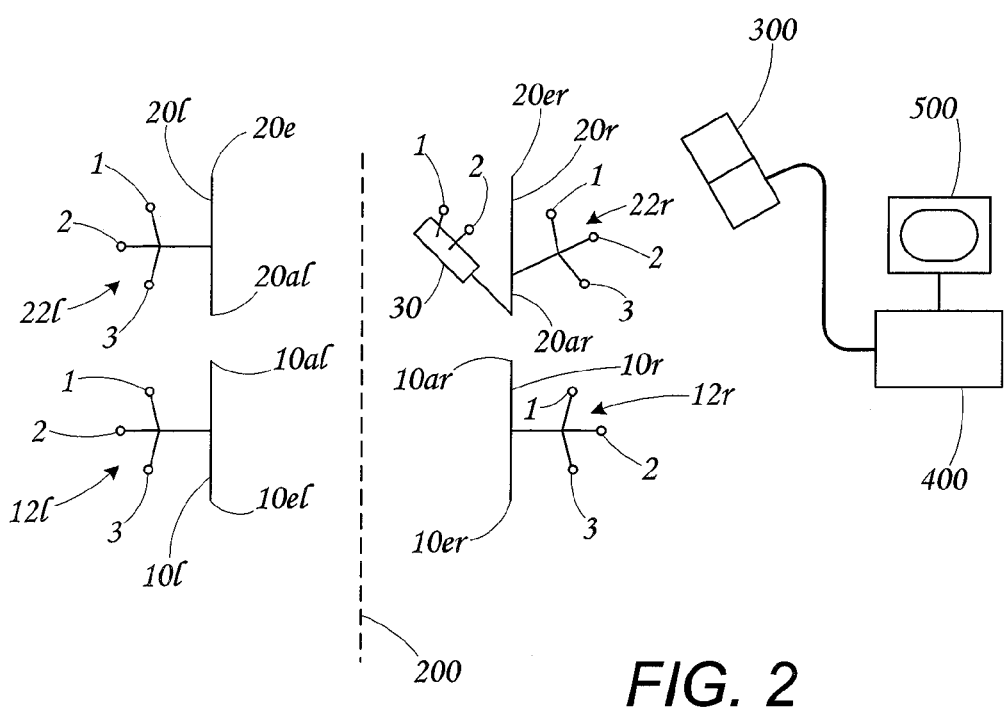
FIG. 2 schematically shows a left and right leg from above, and a navigation system which detects reference stars attached to the legs.

FIG. 2 schematically shows the left and right leg of a recumbent person, as viewed from above. The left femur is indicated by 10*l*, and the left tibia by 20*l*. The right femur is indicated by 10*r*, and the right tibia by 20*r*. The median sagittal plane 200 is indicated by a broken line. The right and left leg are arranged symmetrically with respect to this plane. Marker devices 22*l*, 12*l*, 22*r* and 12*r*, each comprising markers 1, 2 and 3 which are detected by the detection device 300, are situated on each leg. It is assumed that the left knee joint is diseased, i.e. for example, that it has a cruciate ligament rupture and is therefore operated on. In this case, the marker devices (reference stars 22*l* and 12*l*) are preferably fixedly connected to the femur and the tibia. On the healthy right leg, the marker devices (for example, the "ENT headband" 12*r* and 22*r*) are preferably not attached invasively, but are rather for example wound around each of the femur and the tibia by means of a flexible strap. Alternatively or additionally, individual markers can also be adhered onto the femur or the tibia, wherein so-called headbands which are known from head operations can be used.

Preferably, reference frames are assigned to the femur 10*l* and 10*r* and the tibia 20*l* and 20*r*. To this end, a joint-side landmark—preferably, the tibial plateau—is detected by a navigation system at said landmark, i.e. the tibial plateau, preferably by means of a pointer 30, wherein the navigation system detects the markers on the pointer and thus detects the position of the pointer tip. During detection, the anterior-posterior direction is preferably selected as the direction of the pointer 30, such that this direction is also detected by the navigation system. Subsequently, the pointer 30 is then preferably placed halfway up the tibia at the most anterior point, in order to detect this landmark. This landmark is then shifted by the data processing device of the navigation system in the anterior-posterior direction already detected, until a line is intersected which starts from the tibial plateau landmark already detected and is perpendicular to the anterior-posterior direction. This intersection point, together with the tibial plateau landmark, then defines the direction of the tibial axis. This tibial axis can then form one of the axes of the coordinate system associated with the tibia. The other two axes are for example perpendicular to this, wherein one can for example point in the anterior-posterior direction. The lines 20*l* and 20*r* shown in FIG. 2 may be interpreted as portions of the tibial axis which for example start from the tibial plateau point, which for example matches the end point 20*ar*, and extend over a predetermined length, for example from a point 20*ar* to a point 20*er*, wherein the point 20*ar* designates the end facing the joint. Correspondingly, there are end points 20*al* and 20*el* on the left tibial axis 20*l*. The position of the end points in the respective tibial reference frame is therefore also known.

Using the registration process described above, the position of the tibial reference frame relative to the reference stars 22*r* and 22*l* and thus relative to their markers is respectively known, and the respective reference frames are thus registered in the reference frame of the navigation system.

As the next step, the reference frames of the femur then also have to be respectively determined. To this end, the following approach is for example taken. The reference frame associated with the tibia is copied and shifted along the tibial axis, in particular by a predetermined length (for example by referring to the point 20*ar* or 20*al*), in the direction of the femur, such that the origin of the copied reference frame lies in the femur. The copied reference frame thus obtained then becomes the reference frame of the femur. The portions 10*r* and 10*l* shown in FIG. 2 can in particular be part of a coordinate axis of the femoral reference frame which, when the leg is extended, is part of an extended tibial axis. Alternatively, a femoral reference frame can also be defined by detecting landmarks on the femur.

The respective axial portions 20*l*, 20*r*, 10*r* and 10*l* are then registered in the reference frame of the navigation system in the way cited above. In particular, the position of the axial portions relative to each other is known, and end points 10*ar*, 10*er* and 20*ar* and 20*er* of the femoral portion can in particular also be determined, wherein it is for example defined that in the state of extension, a predetermined distance exists between 20*ar* and 10*ar* and/or between 20*er* and 10*er*. It is also possible to determine that a predetermined distance exists between 10*ar* and 10*er* and between 20*ar* and 20*er*. The relative position of the axial portions and also the relative position of the end points can thus be determined by detecting the marker devices 22*l*, 12*l*, 22*r* and 12*r*. The relative position data for the right side and the left side can thus be derived from said detection signal data.

Figure 3:
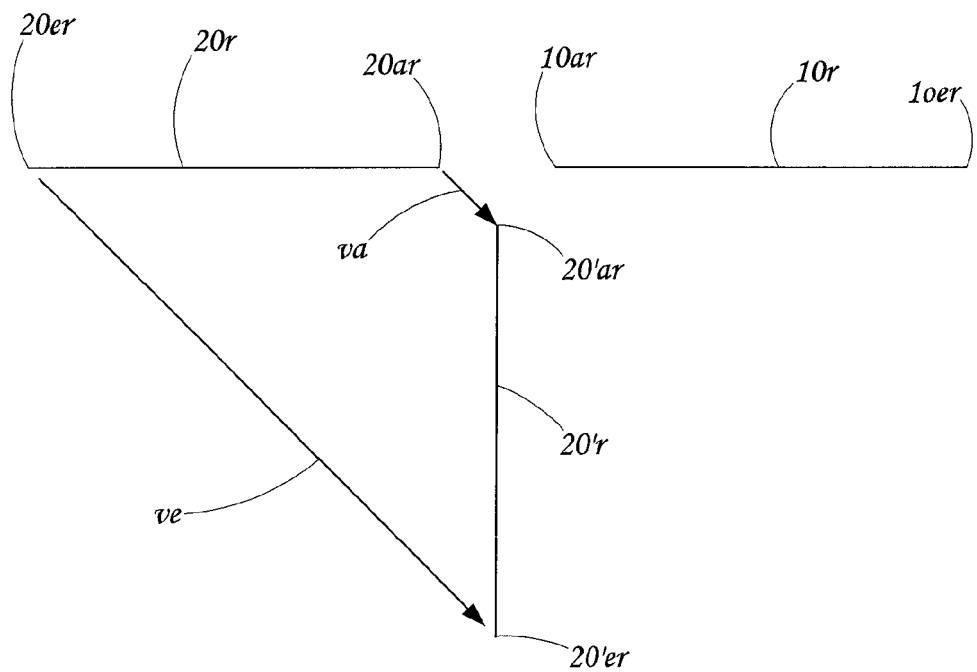
FIG. 3 shows relative vectors being determined for two relative placements.

FIG. 3 shows the transition from 0° flexion to 90° flexion on the right side. The axial portions for 0° flexion (extension) are indicated by 10*r* and 20*r*. The axial portions for 90° flexion are indicated by 10*r* and 20'*r*. The relative position between 10*r* and 20'*r* is detected by means of marker devices, and the detection signals are for example fed to a data processing device 400 (see FIG. 2). As described above, the relative position between 10*r* and 20*r* is already known. Correspondingly, it is also possible to determine the position of the end points 20'*ar* and 20'*er*. Thus, as a whole, relative vectors va and ve can be determined from the available data. The relative vector va points from the end point 20*ar* to the end point 20'*ar*. The relative vector ve points from the end point 20*er* to the end point 20'*er*. This merely represents one example. Another approach would for example be to determine relative vectors from the end points 10*ar* to the end point 20'*ar* and from the end point 10*er* to the end point 20'*er*. The change in the position could also be described using angles, for example the 90° angle, and by the plane in which the distance portions 20*r*, 20'*r* and 10*r* lie. The invention is described in the following, by way of example, with the aid of the aforesaid vectors va and ve.

Figure 4:
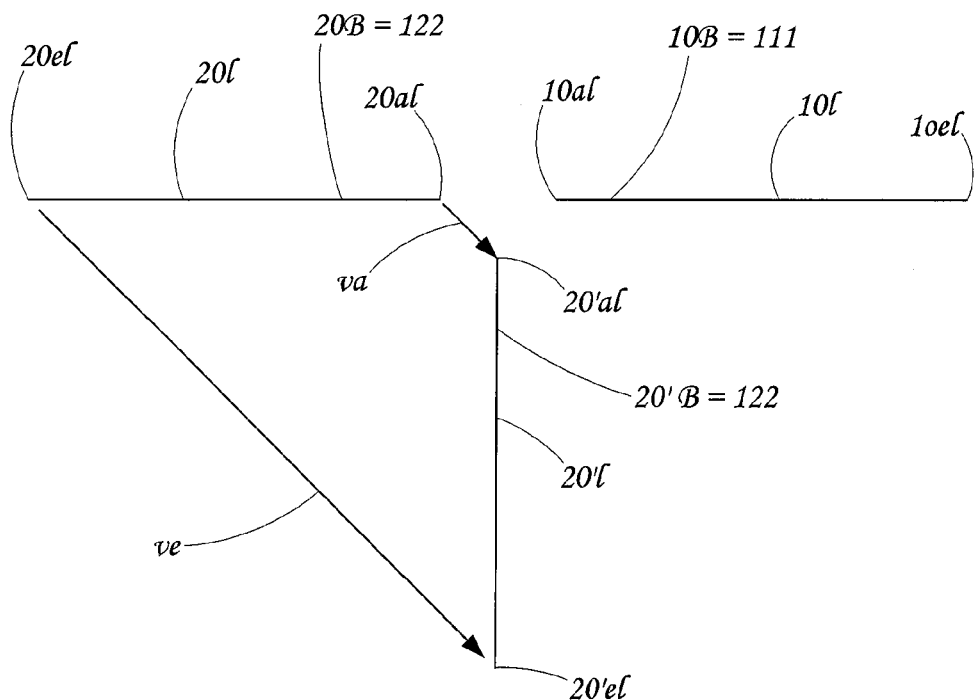
FIG. 4 shows the determined relative vectors being used to calculate the relative position of the left lower leg.

As shown in FIG. 4, the leg is in extension in the known initial placement, i.e. the position of the leg is described by the distance portions 10*l* and 20*l*. The aforesaid vectors va and ve, which have already been calculated, are used to then calculate what the relative position of the left leg would look like at 90° flexion, without actually moving the left leg into 90° flexion. The vector va is positioned at the end point 20*al*, in order to point to the end point 20'*al*. The vector ve is positioned at the end point 20*el*, in order to point to the end point 20'*el*. This means that it is assumed that the left tibia performs the same movement relative to the left femur as the right tibia performs relative to the right femur. In the aforesaid example, it has been assumed that the movement is performed in a plane which is parallel to the median sagittal plane. The movement can of course also contain components which deviate from this exact parallelism. This case can be dealt with in accordance with the invention by taking into account symmetry rules. This is illustrated in the following on the basis of an example as shown in FIG. 5.

Figure 5:
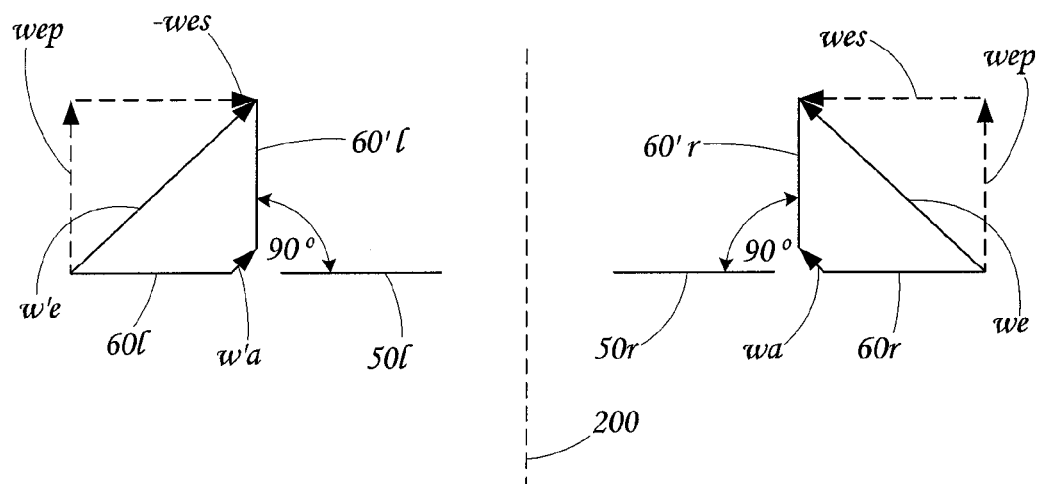
FIG. 5 shows the invention being applied to the left and right arm.

FIG. 5 is for example intended to be a view from above onto an upright patient who is raising his right and left arm. 50*l* designates the left upper arm which is dorsally stretched out perpendicular to the median sagittal plane, and 50*r* designates the right upper arm which is dorsally stretched out perpendicular to the median sagittal plane 200. The left lower arm 60*l* is situated in an extension of the left upper arm 50*l*, and the right lower arm 60*r* is situated in an extension of the right upper arm 50*r*. The placements of 50*l* relative to 60*l* and of 50*r* relative to 60*r* are in turn each detected using marker devices, and the axial portions 50*l* to 60*l* and 50*r* to 60*r* are in turn each detected using a pointer, such that in analogy with the method described in FIG. 2, they are known in a reference frame, in particular in the reference frame of the navigation system. It is also assumed that the right side is the healthy side, i.e. the right elbow joint is healthy, while the left elbow joint is diseased. While 50*r* and 60*r* together form the first second-side relative placement, 50*r* and 60'*r* form the second second-side relative placement, for which the relative position between 50*r* and 60'*r* is likewise again determined by means of marker detection. It is in particular also possible to determine the relative positions between end points of the distance portions 50*r* and 60'*r*. By comparing the position of these end points, relative vectors we and wa can be determined in an analogous way to FIG. 3. These relative vectors can then be broken down into components parallel to and perpendicular to the median sagittal plane. The parallel component of we is indicated by wep, and the perpendicular component is indicated by wes. The perpendicular components are parallel to the frontal plane. As described above, it is assumed that the first second-side relative position comprising the axial portions 50*r* and 60*r* is symmetrical with respect to the first first-side relative position, which is described by 50*l* and 60*l*, relative to the median sagittal plane 200. Given this presupposition, the relative vector w'e for the left side, which is calculated from wep-wes, is determined from the vector we and in particular from the components wes and wep. It thus follows that the resultant vector w'e is symmetrical with respect to the vector we, relative to the median sagittal plane. Correspondingly, a vector w'a is also calculated which is symmetrical with respect to the vector wa. The symmetrical vector w'e is then positioned at the end of the axial portion 60*l* which faces away from the elbow joint, and the relative vector w'a is positioned at the end of the axial portion 60*l* which faces the elbow joint. The tips of the two vectors then point to the respective ends of the axial portion 60'*l* which is pivoted (by 90°), such that the position of the axial portion 60'*l* results, wherein the symmetry rules have been considered. The position of the axial portion 60'*l* thus designates the position of the left lower arm, assuming that the latter is moved symmetrically with respect to the right lower arm and is thus likewise bent or pivoted by 90°. It is thus possible to determine how the left lower arm would lie at 90° flexion, if the left elbow joint exhibited kinematic symmetry with respect to the right elbow joint and likewise behaved like a healthy joint.

In addition to the aforementioned examples of 90° flexion, other degrees of flexion are of course also possible, such as in particular 30°, 20° or 60°. The change in the relative position can also be mathematically described in ways other than by means of vectors as described above, such as for example by using angles and planes in which the movement is to be performed.

The calculation is based on the aforementioned relative position data, assuming in particular that it was acquired in the neutral position of the respective body parts. For the leg, it is for example the case that in extension, the tibia is twisted relative to the femur in a way which allows a small clearance in a relative rotation of the tibia relative to the femur. In other relative positions, for example 30° flexion or 90° flexion, this way of twisting is not given. This applies in particular to the diseased leg (cruciate ligament rupture), for which reason virtually flexing the diseased leg in accordance with the invention is regarded as advantageous. For the healthy leg, the tibia is rotated relative to the femur in order to define the second or subsequent relative placements, i.e. in order to define the respective neutral placement, and the average value of the two extreme rotational angles (maximum internal rotation and maximum external rotation) is selected as the neutral placement. As already stated, this is not possible with the diseased leg, in particular the cruciate ligament rupture, because in this case, the cruciate ligament no longer limits the rotational angles for the internal and external rotation.

In order to find regions which fulfill a particular condition, i.e. for which a relative variable is for example constant, it is possible to proceed as described in the following. A particular region 20'B is for example designated using a pointer (see FIG. 4), said region for example being suitable as a joint-side end of a drilling through the tibia, in order to guide a strap 100 (see FIG. 1) through it. A region 10B (see FIG. 4) is for example also determined by means of a pointer, said region likewise for example being situated in the vicinity of the joint-side end of the femur. In the example shown in FIG. 4, the regions 20'B and 10B lie on the respective axial portions. This is purely by way of example. In practice, they can perfectly well lie outside the axial portion. One example of the region 20'B is the region 122 shown in FIG. 1. This has been correspondingly marked in FIG. 4. One example of the region 10B is the region 111 in FIG. 1.

Using the pointer, the relative position of the regions 20'B and 10B relative to the coordinate system of the tibia and the femur is known. In particular, positions relative to the end points 20'a*l* and 20'e*l* as well as 10a*l* and 10e*l* are for example also known.

In accordance with the invention, the leg can then be moved purely virtually. The tibia is for example moved from the position indicated by 20'*l* to the position 20*l* (see FIG. 4). Other intermediate positions can also be occupied. As a whole, this therefore results in at least two relative placements for which the relative position between the region 20'B and the region 10B can be calculated. It is in particular possible to check whether the distance for the different relative placements is the same or changes. If the distance changes, then this can be displayed and a surgeon can then for example move the pointer in order to find a new region on the femur which is for example likewise in the vicinity of the joint and which fulfils the desired condition.

As mentioned above, the position of the left diseased leg at 90° flexion is not reliable. However, it can be advantageous in this placement to tap regions between the joint using the pointer, since it is easier at 90° flexion to get the pointer between the femur and the tibia. In order to still have a defined placement at 90° flexion for the tibia, it is possible to check—by means of the marker device attached to the tibia—whether this 90° flexion placement matches the calculated 90° flexion placement (the neutral placement at 90° flexion). If there is a match, this can then be displayed and the surgeon can then tap the regions using the pointer in this 90° flexion placement which has been identified as a neutral placement. Alternatively or additionally, it is possible—by detecting the marker device attached to the tibia—to calculate where the region tapped using the pointer would lie if the tibia occupied a calculated relative placement and/or the first first-side relative placement. In this way, it is possible to calculate—for each position of the pointer—whether the distance between 20'B and 10B is equal to the distance between 20B and 10B, without moving the leg. This can of course also be calculated for a plurality of relative placements. The pointer is for example moved to different points 10B, and the display 500 of the navigation system 300, 400 and 500 displays if the distance is the same or for example deviates by less than a predetermined percentage for the different calculated relative placements.

The present invention is also suitable for checking the movement and relative placements of a diseased joint by comparing them with movements and relative placements of the healthy joint. It is in particular possible to detect and store a plurality of relative placements for the healthy joint and to calculate a movement trajectory from these. Using the method in accordance with the invention, corresponding (kinematically symmetrical) relative placements and movement trajectories can then be calculated for the side of the body comprising the diseased joint. It is then possible to check, on the basis of the marker devices attached (invasively or non-invasively) to the diseased side, whether the movement trajectory is kinematically symmetrical with respect to the healthy joint or whether a kinematically symmetrical placement has been occupied. It is thus in particular also possible to identify whether the movement trajectory corresponds to a healthy trajectory. Cruciate ligament ruptures can thus for example also be identified.

In addition to the median sagittal plane 200 described above, other symmetry planes or symmetry axes can also be adduced when determining the second first-side relative placement. If, for example, the external rotation and internal rotation of a joint is considered, the axis about which the rotation is performed can likewise be regarded as a symmetry axis. If this is determined for both sides, then an external rotation of the second second-side joint, for example the right tibia, by a particular angle in a particular direction of rotation can for example be converted into a corresponding external rotation of the second first-side body part, i.e. for example the left tibia, by the same angle in the opposite direction of rotation, by applying the symmetry considerations. The tibial axis which has already been determined can for example be adduced as the symmetry axis of rotation for the respective side.

The navigation system in accordance with the invention is likewise schematically shown in FIG. 2. The detection device 300 detects signals from the marker devices 22*r*, 12*r*, 10*l* and 22*l* and relays the detection signals to the data processing device 400, which performs the method in accordance with the invention and displays display signals on the monitor 500.

FIG. 5 can also be adduced as an example of another embodiment of the invention, in which the positions of the right and left upper arm and lower arm are given, and one wishes to determine whether the transition from full extension to 90° flexion is symmetrical for both sides. To this end, it is possible to simply mirror the relative vectors of one side, which represent a relative variable which describes the relative position, at the median sagittal plane 200, i.e. the vectors we and wa, which are situated on the right side, describe the placement relative position of the right lower arm between the position in the placement before extension and the position in the placement at 90° flexion. The vectors we and wa can then be mirrored on the median sagittal plane. The mirrored vectors are the vectors w'a and w'e, which describe what the placement relative position on the left side would look like if the body is ideally symmetrical, i.e. they describe the placement relative position as mirrored from right to left.

It is assumed in the example shown in FIG. 5 that first-side body part data is predetermined which describes the position 60*l* for the left lower arm in full extension and the position 60'*l* at 90° flexion. In this case, the mirrored relative vector w'e is identical to a relative vector which is situated on the left side and connects the end of the axial portion 60*l* to the end of the axial portion 60'*l*. The mirrored vector w'a is identical to the vector which connects the start of the axial portion 60*l* to the start of the axial portion 60'*l*. The arrangement shown in FIG. 5 would accordingly be ideally symmetrical, from full extension to 90° flexion, with respect to the placement relative position of the lower arm. In reality, deviations may of course occur, which can be visualized by displaying the mirrored relative vectors and the actual relative vectors on the left side. It is in particular possible to calculate variables which represent a value for the existing symmetry in the transition from full extension to 90° flexion, from the difference between the mirrored vectors and the relative vectors existing on the left side.

Figure 6:
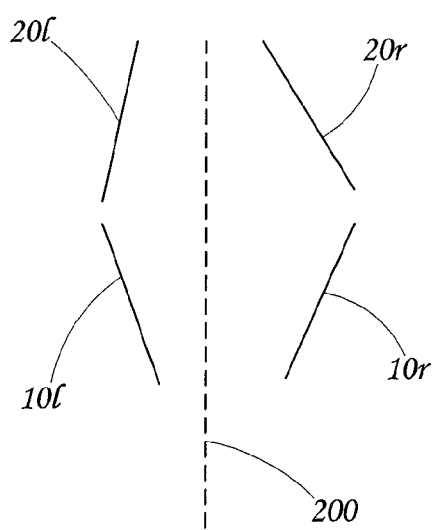
FIG. 6 shows a scenario in which an ideal symmetry is not given.
Figure 7:
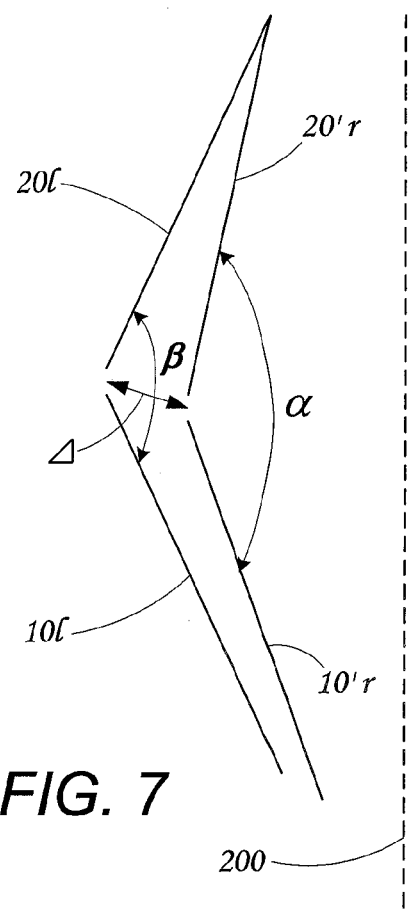
FIG. 7 shows the situation from FIG. 6, with a mirrored femur and a mirrored tibia.

FIG. 6 shows a scenario in which such ideal symmetry is not given. The right and left leg are intended to be in extension. The patient has a varus of different magnitudes of extent. The varus on the right side is more pronounced than on the left side. In order to be able to determine the deviation between the right-side varus and the left-side varus, the femur 10r and the tibia 20r are mirrored on the median sagittal plane 200 in accordance with the invention, such that the situation shown in FIG. 7 results. The mirrored right tibia is indicated by 20'r, and the mirrored right femur is indicated by 10'r. The left femur is indicated by 10l, and the left tibia is indicated by 20l. In one embodiment in accordance with the invention, distance portions 20'r, 10'r, 10l and 20l are displayed on a monitor, in order to provide an indication of deviations from an ideally symmetrical arrangement of the body parts. It can in particular be seen that the non-mirrored left body parts deviate in their position from the mirrored right body parts. This deviation can also be described by relative variables. An angle α between the mirrored distance portions 20'r and 10'r can for example be determined. A corresponding angle can be determined between the distance portions 20l and 10l. The angular difference then represents a relative variable which provides an indication of how pronounced a deviation from the ideally symmetrical arrangement of the body parts which is given is. Alternatively, a distance Δ can also be determined which for example connects the end points of the distance 10r and 10'r which are respectively closest to the distance 20l and 20'r. The greater the distance Δ, the greater the deviation from the ideally symmetrical arrangement.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for calculating the position of body parts, taking into account anatomical symmetry,
   wherein a first and second first-side body part are provided on the first side of an anatomical body and connected by a first-side movable joint, said first-side moveable joint enabling movement of the first first-side body part relative to the second first-side body part,
   wherein a first and second second-side body part are provided on the second side of the anatomical body and connected by a second-side movable joint, said second-side movable joint enabling movement of the first second-side body part relative to the second second-side body part,
   said method comprising the steps of:
   providing second-side relative position data which describes the relative position of the first second-side body part relative to the second second-side body part for each of a first and a second second-side relative placement due to movement of at least one of the first or second second-side body part about the second-side movable joint;
   providing first-side relative position data which describes the relative position of the first first-side body part relative to the second first-side body part in a first first-side relative placement; and
   calculating, using a processor, the position of the first first-side body part relative to the second first-side body part in a second first-side relative placement, on the basis of the first-side relative position data and the second-side relative position data, wherein it is taken into account that the second second-side relative placement is symmetrical with respect to the second first-side relative placement.

2. The method according to claim 1, wherein the second first-side relative placement is calculated on the basis of the assumption that the first first-side relative placement is symmetrical with respect to the first second-side relative placement and/or the first-side and second-side relative position data comprises the positions of the first and second first-side and second-side body parts for the first and second second-side relative placement and for the first first-side relative placement and the position of the first first-side body part in the second first-side relative placement and the position of a body symmetry plane.

3. The method according to claim 1, wherein in order to determine the second first-side relative placement, symmetry rules are applied which take into account the symmetry of the movement of the first-side body parts about the first-side joint with respect to the movement of the second-side body parts about the second-side joint.

4. The method according to claim 1, wherein the position of symmetry planes and/or symmetry axes of the body is provided or determined, with respect to which the movement of the joint is symmetrical, wherein the second first-side relative placement which is symmetrical with respect to the second second-side relative placement is determined on the basis of the determined or provided symmetry planes and/or symmetry axes in conjunction with the symmetry rules.

5. The method according to claim 1, wherein region data is provided which describes the relative position of a first region of the first first-side body part relative to a second region of the second first-side body part, wherein a first relative variable which indicates the position of the first region relative to the second region, is calculated from the region data for the first first-side relative placement, and a second relative variable is calculated from the region data for the second first-side relative placement.

6. The method according to claim 5, wherein the region data is calculated from the position of the first and/or second region in another first-side relative placement which does not match the first first-side relative placement or the second first-side relative placement, wherein the first and/or second region data is calculated on the basis of the position of the first body part and/or second body part in the other first-side relative placement relative to their position in the first and/or second first-side relative placement.

7. The method according to claim 5, wherein the region data changes and is compared during the process of changing, wherein it is displayed when the first and second relative variables are within a predetermined value of one another.

* * * * *